United States Patent [19]
Nazare et al.

[11] Patent Number: 5,603,404
[45] Date of Patent: Feb. 18, 1997

[54] SHARPS CONTAINER

[76] Inventors: Raymond Nazare; Donna M. Nazare, both of 22647 Ventura Blvd. #126, Woodland Hills, Calif. 91364; William L. Gottsegen, 16337 Celinda Pl., Encino, Calif. 91436

[21] Appl. No.: 535,971
[22] Filed: Sep. 29, 1995
[51] Int. Cl.$^6$ ................................................ B65F 1/16
[52] U.S. Cl. ........................ 206/366; 206/1.5; 220/254; 220/908
[58] Field of Search ................................. 220/481, 254, 220/908; 206/365, 366, 1.5

[56] References Cited

U.S. PATENT DOCUMENTS

| | | | |
|---|---|---|---|
| 4,715,498 | 12/1987 | Hanifl | 206/366 |
| 5,046,614 | 9/1991 | Torres et al. | 206/366 |
| 5,154,345 | 10/1992 | Shillington | 206/366 X |
| 5,423,450 | 6/1995 | Shillington et al. | 206/366 X |

*Primary Examiner*—Jacob K. Ackun
*Attorney, Agent, or Firm*—Gene W. Arant; Ralph D. Chabot

[57] ABSTRACT

A sharps container having a receptacle, cover and tray and providing an improved locking mechanism to resist unauthorized tampering. The locking mechanism also incorporates a means to rotate the tray into a locking position thereby closing the container. When the locking mechanism is actuated, the container is permanently closed and the locking mechanism itself is displaced into the container interior so that the top surface of the locking mechanism is flush with the adjacent exterior container surface. The present invention also provides for hands-free disposal of sharps through the use of an offset balanced tray biased into an open, receiving position. The receptacle section is designed to be stackable for more efficient packaging and shipment. The container also incorporates viewing windows to permit visual inspection of the container interior to properly determine when the container full and ready for disposal. The container is also designed to be attached to a wall through the use of mounting brackets.

9 Claims, 5 Drawing Sheets

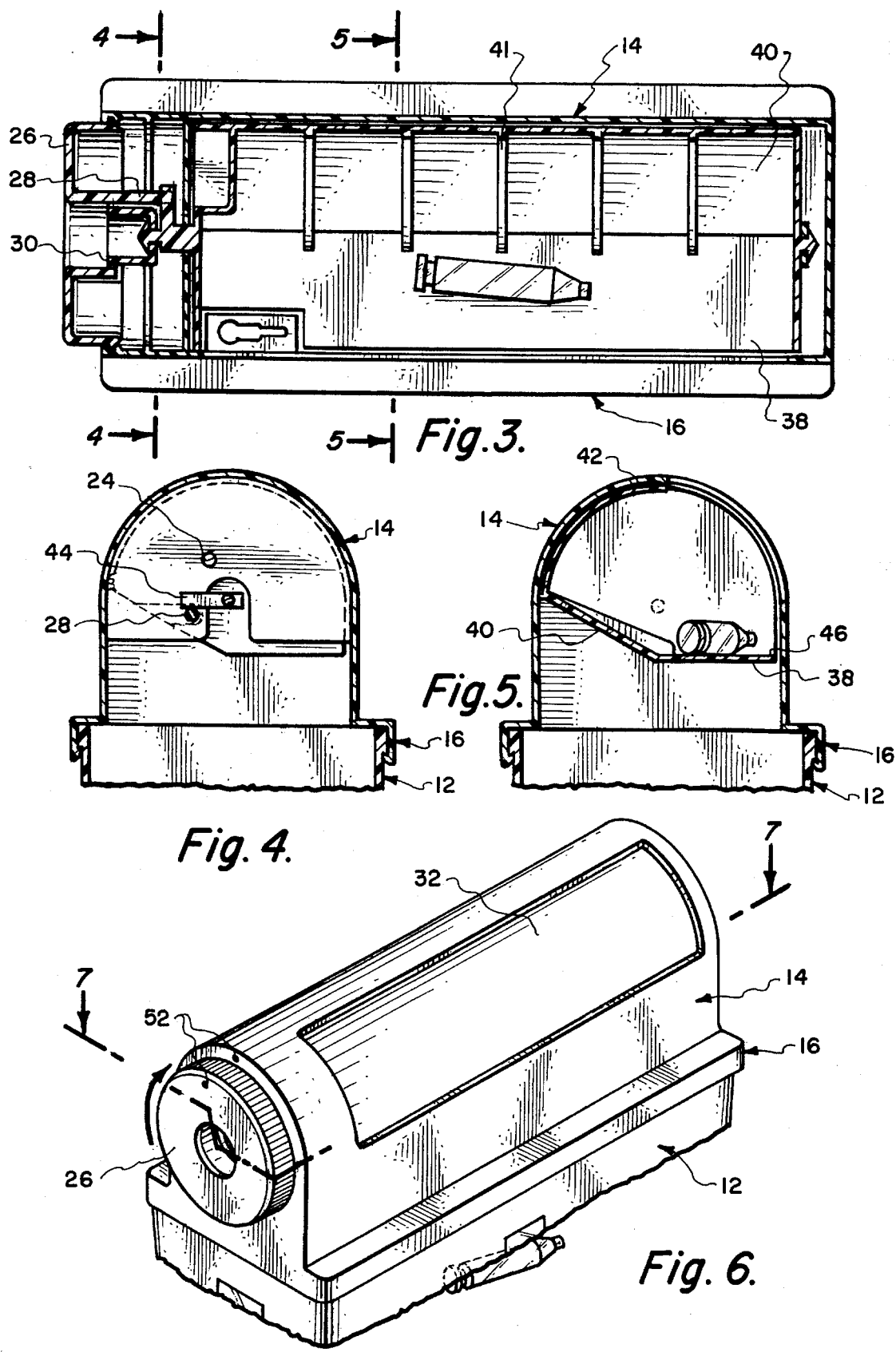

SHARPS CONTAINER

BACKGROUND OF THE INVENTION

This invention relates to a sharps disposal container, i.e. an apparatus used in hospitals for disposing sharp items such as used syringes and hypodermic needles. Many hospitals require and various government agencies recommend that a separate sharps disposal container be placed in each patient and emergency room. Such policy promotes the quick and efficient disposal of used syringes and other sharp items thereby diminishing the chances of potential injury or infection caused by these items to patients or hospital staff. When the disposed material within the container reaches a determined level, the container can be first permanently locked and thereafter removed from the hospital room and disposed.

With the present concerns surrounding an accidental transmittal of the HIV virus and syringe reuse by intravenous drug users, a typical sharps disposal container is designed not only to permit disposal but also to prevent theft of any objects deposited therein. Because of the trend toward placement of sharps disposal containers in each patient's room as discussed above, it is an important consideration to manufacture these containers at an economical price while providing an appropriate level of protection to patients, hospital staff and other individuals alike.

SUMMARY OF THE INVENTION

The present invention addresses the above mentioned concerns and provides a sharps disposal unit that is easy to manufacture and assemble, is puncture resistant, provides hands-free operation for depositing objects within the unit and a novel locking mechanism for permanently and irreversibly locking the unit which will resist attempts to retrieve disposed material contained within.

More particularly, the invention provides a sharps disposal unit comprising a container having a receptacle and a cover. The receptacle and cover are shipped unassembled; the body of the receptacle is tapered so that multiple receptacles can be stacked within one another to provide a more efficient method for packaging and shipment. The receptacle and the cover include a permanent interlocking means so that once assembled, the receptacle can not be separated from the cover.

The cover, which forms the upper portion of the container, is of a generally semi-cylindrical shape and includes an opening which permits access to an elongated tray. The opening can be of any geometrical configuration and area which would permit the easy deposition of a syringe onto the tray. More preferably, the opening is made in a generally rectangular shape. The tray is biased to an open or receiving position by the tray itself having an offset center of gravity. The tray is also designed to be rotatably responsive along its longitudinal axis to an object weighing as little as 2 grams which is placed upon the tray. Once an object is placed upon the tray, the tray will rotate due to the center of gravity change and provide access for the object to the container interior, thereby permitting the object to gravitate or fall into the interior. While the tray is rotating, the opening which permits access to the tray is partially obstructed by a sliding door rotating into view from under the cover thereby reducing direct access to the container interior. The sliding door is preferably an integral part of the tray member. As described, the disposal of material into the sharps container becomes a "hands-free" operation.

The opening ill the cover is configured to permit disposal of a syringe or similar shaped objects only by horizontal placement onto the tray. An object placed horizontally on the tray and thereafter displaced into the receptacle will tend to remain in a horizontal position after displacement. The displaced objects will then tend to be stacked uniformly thereby permitting a more efficient usage of the receptacle interior.

Another unique feature of the invention is the locking means for selectively and permanently locking the tray in a closed position when the receptacle is ready for disposal. In the preferred embodiment, the locking means includes a rotatable, moveable dial, with the tray being rotatably responsive to the rotation of the dial. The dial is used to rotate the tray and its sliding door member into a locking position whereafter, the dial is displaced into the cover so that its top exterior surface is substantially flush with the adjacent surface of the outside cover. Additionally, as the dial is displaced into the cover, a locking pin attached to the dial is displaced into an aperture disposed in the cover thus preventing any rotation of the tray back to the open or receiving position. During the dial displacement into the cover, a circumferential ridge on the dial passes a shoulder positioned on the interior surface of the cover. This shoulder permits movement of the dial and its circumferential ridge into the cover but prevents movement in the opposite direction. Further, the annular space or clearance between the side surface of the dial and the cover surface is minimal. This minimal clearance together with the dial exterior surface being essentially flush with the adjacent outside cover surface and the above mentioned shoulder/ridge relationship provide additional protection against tampering of the locked mechanism and possible access to the container interior.

The locking mechanism is designed so that it can not be actuated by mistake. It must first be rotated into locking position before the locking mechanism can be operated.

The preferred embodiment has the tray designed in a generally semi-cylindrical configuration with a flat receiving surface member, a weighted member and a sliding door member extending away from the weighted surface member from a side opposite from the flat receiving member. When the dial is rotated to the locking position, the tray and particularly its sliding door member is correspondingly rotated to completely isolate the cover opening from communication with the cover interior. Additionally, the sliding door member has a longitudinal ridge. During the rotation of the tray into locking position, the longitudinal ridge comes into frictional contact with the inside surface of the cover and the user will experience some resistance while rotating the dial. The user will normally exert a small additional force in rotating the dial so that the ridge will overcome this frictional contact with the inside cover and rotate into view at the upper end of the cover opening. While rotating the dial, the user will also hear a sound similar to a snap when the ridge becomes free of frictional engagement with the inside cover surface. The ridge now is in position where its height is greater than the clearance between the sliding door surface and the inside cover surface thereby preventing rotation of the sliding door back underneath the cover and exposing the cover interior. Such a configuration, along with the locking mechanism actuated as described above, further prevents the tray from rotating back into an open position.

Most sharps containers are designed to be attached to a wall through the use of mounting brackets. Mounting a sharps container prevents it from being accidentally knocked over causing inadvertent spillage. The present invention incorporates the use of any standard mounting bracket design and is also designed to be adaptable for use in existing mounting brackets which will minimize the cost of installation.

The locking mechanism can be operated while the container is attached to the wall or after it is removed. It is recommended, however, that the locking mechanism be operated while the container is mounted to the wall. This procedure will ensure that the container will be permanently closed prior to removal and eliminate any chance of spillage as noted above.

The container also incorporates the use of a needle extractor to hold a needle while it is being detached from its holder and thereafter permitting the needle to drop into the container without being touched. Preferably, the extractor is an integral component of the cover but is located such that when the container is permanently locked, the extractor is behind the sliding door and within the container.

The receptacle incorporates the use of a viewing window to assist in visually determining the level of disposed material within the sharps container. Preferably, a window is located on each of three sidewalls.

Preferably, the container, cover and tray are all molded by conventional plastic injection methods. In the most preferred embodiment, a propylene random co-polymer is used as the plastic injection material.

Other features and advantages of the invention will become apparent to those skilled in the art upon review of the following detailed description and claims.

DESCRIPTION OF THE DRAWINGS

FIG. 3 is a cross-sectional view of the invention taken along line 3—3 in FIG. 1.

FIG. 4 is a cross-sectional view of the invention taken along line 4—4 in FIG. 3.

FIG. 5 is a cross-sectional view of the invention taken along line 5—5 in FIG. 3.

FIG. 6 is a perspective view of the cover of the invention having the tray rotated by the dial into locking position.

DETAILED DESCRIPTION OF THE PREFERRED EMBODIMENT

Figure 1:
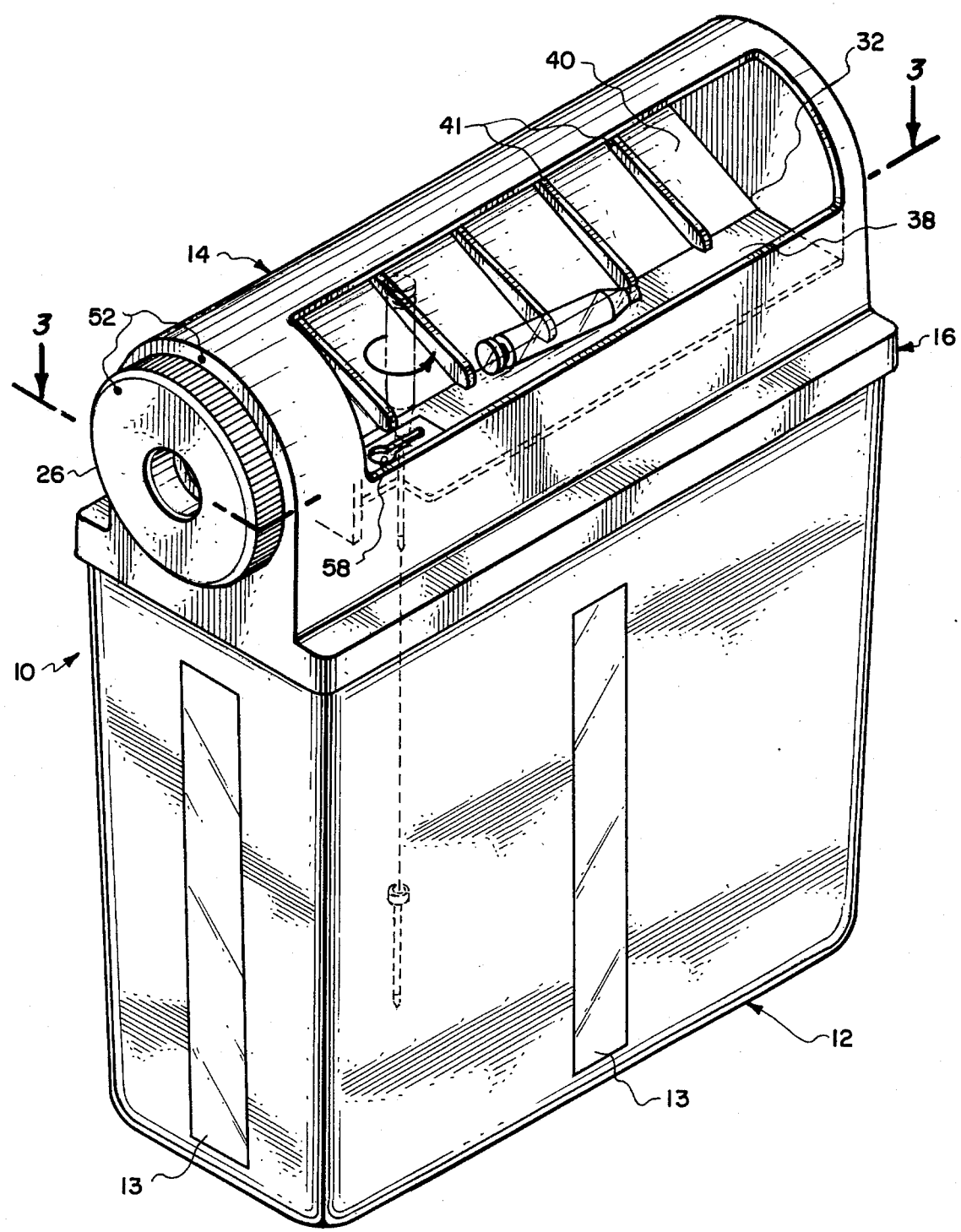
FIG. 1 is a perspective view of the invention.

FIG. 1 illustrates the overall structure of the sharps container 10 of this invention. The container 10 includes a receptacle 12 made of a puncture resistant material and a cover 14 made of a similar material. The receptacle 12 has a viewing window 13 made of a puncture resistant material on three of its sidewalls to permit visual observation of the amount of disposed material present within container 10. Container 10 is designed to be attached to a wall by the use of mounting brackets (not shown) with the sidewall facing the mounting wall not incorporating a viewing window 13. Upon a visual determination that container 10 is full, container 10 can be permanently locked in a manner to be discussed below and thereafter disposed.

Figure 2:
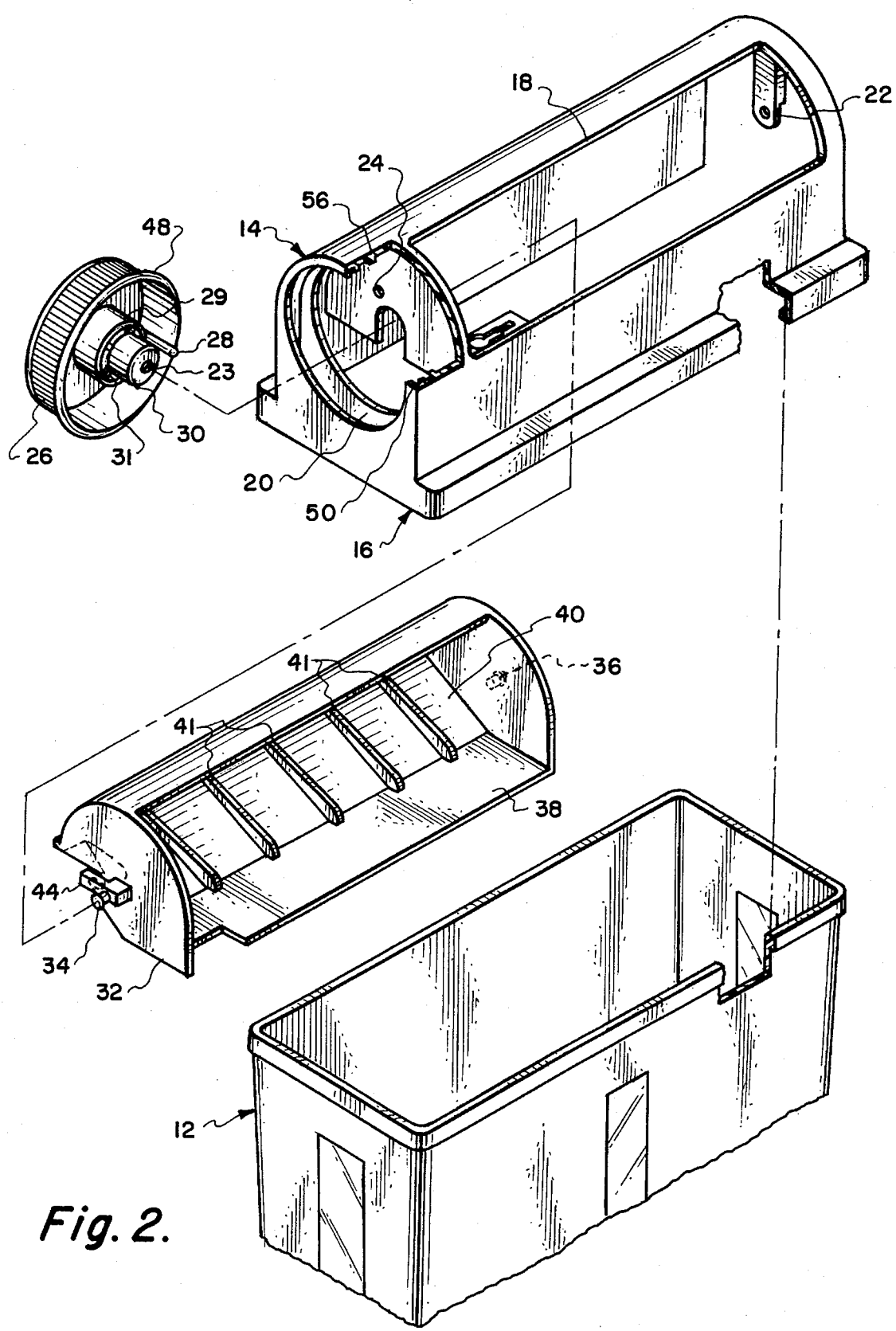
FIG. 2 is an exploded perspective view of the invention.
Figure 7:
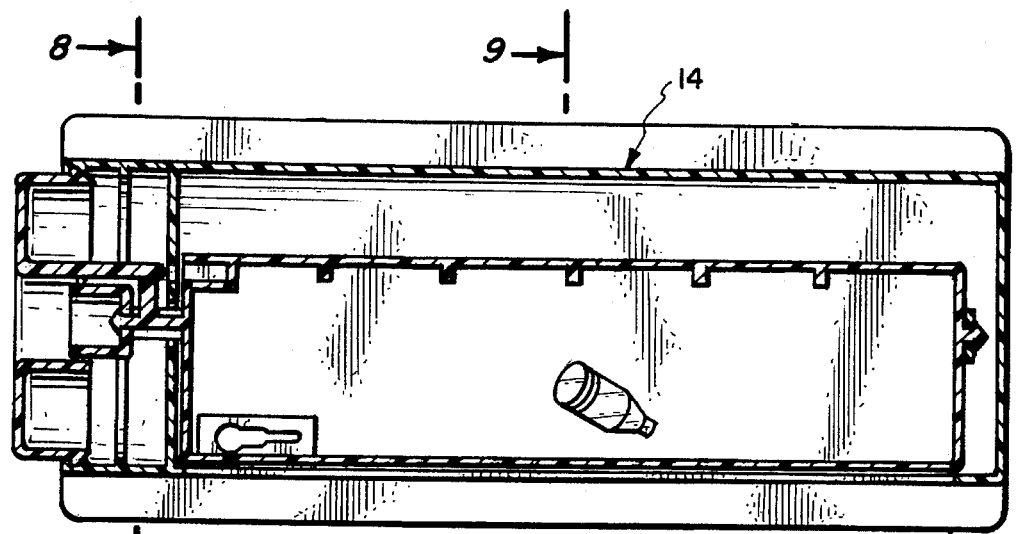
FIG. 7 is a cross-sectional view of the invention taken along line 7—7 in FIG. 6.
Figures 8, 9:
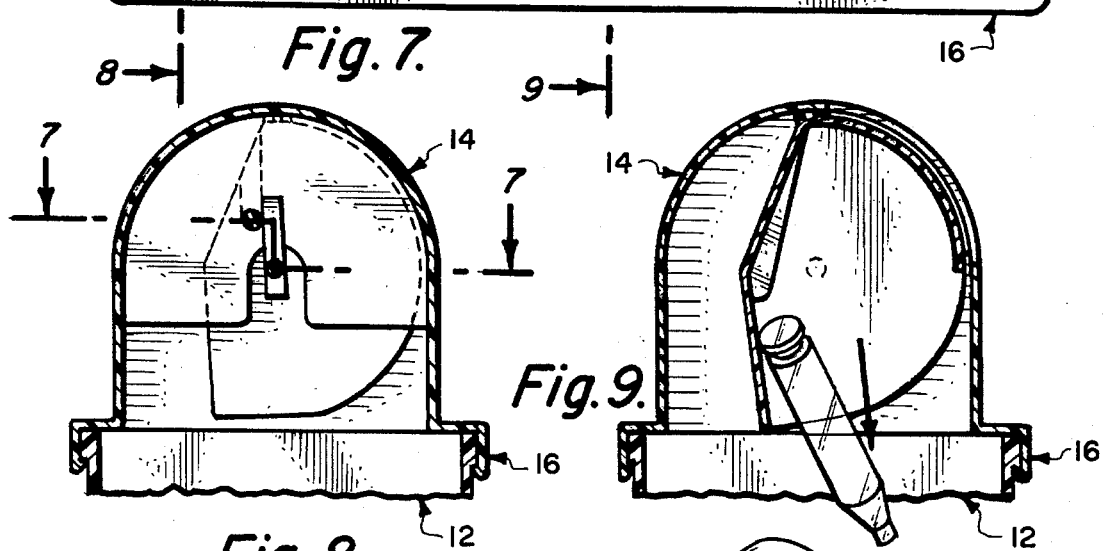
FIG. 8 is a cross-sectional view of the invention taken along line 8—8 in FIG. 7.
FIG. 9 is a cross-sectional view of the invention taken along line 9—9 in FIG. 7.

Cover 14 is depicted more clearly in FIG. 2. Cover 14 is shaped substantially in a horizontal cylindrical configuration and has a base 16 for attachment to receptacle 12. Cover 14 further has a substantially rectangular opening 18, a dial recess 20 located on one end and a pivot pin recess 22 located on the opposite end of cover 14. A locking pin aperture 24 is located at the base of the dial recess 20. Cover 14 also incorporates a needle extractor 58 which extends perpendicularly into the cover interior from the base of opening 18. Needle extractor 58 and its operation can be depicted more clearly in FIG. 1.

A dial 26 has an outside diameter slightly less than the inside diameter of dial recess 20. Dial 26 has a locking pin 28, a dial cylinder receiving recess 29 and a dial cylinder 30 extending away from its back side. More specifically, dial cylinder 30 is attached to the top of dial cylinder receiving recess 29 by a plurality of frangible connectors 31.

A tray 32 substantially semi-cylindrical in shape has a pair of pivot pins 34 and 36 having a common axis of symmetry, each extending away from the outside surface of each end of tray 32. Tray 32 further comprises a flat receiving member 38, a weighted member 40 and a sliding door member 42. Receiving member 38 and weighted member 40 are joined along the pivoting axis of tray 32 and diverge from one another at an angle which is less than 180 degrees. Sliding door member 42 is joined to weighted member 40 opposite of receiving member 38. A plurality of ribs 41 are integral with weighted member 40 which causes weighted member 40 to be heavier than receiving member 38. The pivoting characteristic of the invention will be more fully described below. Disposed between pivot pin 34 and tray 32 is a guide bar 44 integrally molded and which will be explained further below.

The cover 14 is assembled in the following manner:

Tray 32 is disposed within cover 14 such that pivot pin 36 is inserted into pivot pin aperture 22 and that the edge of receiving surface 38 is below a shoulder 46 extending inward from cover 14 where it defines the base of opening 18. Receiving surface 38 has a radius away from the pivoting axis which is less than the distance from the pivoting axis to the inside surface of cover 14 but greater than the distance from the pivoting axis to shoulder 46. When tray 32 is positioned within cover 14 and the edge of receiving surface 38 is contacting shoulder 46, weighted surface 40 is in an inclined position relative to receiving surface 38. Receiving surface 38 and guide bar 44 are essentially in a horizontal position. The position of guide bar 44 is essential for the proper function of alignment marks 52 when dial 26 will be used to rotate tray 32 into locking position as will be discussed below. The inclined position of weighted member 40 will cause an object inadvertently placed on its surface to displace onto receiving member 38 by force of gravity.

Dial 26 is inserted into dial recess 20 in a manner such that locking pin 28 is positioned below guide bar 44 and pivot pin 34 is inserted into pivot pin recess 23 of dial cylinder 30. As dial 26 is partially inserted into dial recess 20, a ridge 48 about the circumference of dial 26 is displaced past a first dial recess shoulder 50. Shoulder 50 permits movement of ridge 48 into cover 14 but prevents movement of ridge 48 in the opposite direction.

Cover 14 is permanently attached to the top of receptacle 12 using a male/female snap fit configuration although any attachment means for permanently connecting receptacle 12 and cover 14 could be used in the alternative.

The container 10 now assembled, functions in the following manner:

The additional weight on weighted member 40 from ribs 41 and sliding door 42 will tend to pivot tray 32 so that receiving member 38 is biased into contact with shoulder 46. Receiving member 38 is configured to permit direct access from needle extractor 58 to the interior of receptacle 12 when it is biased into contact with shoulder 46. An object placed upon receiving member 38 will tend to overcome the bias caused by weighted member 40 and begin to pivot receiving member 38 away from shoulder 46. As the distance between the edge of receiving member 38 and shoulder 46 increases, access for the object to the interior of receptacle 12 increases. The pivoting action will also cause gravity to displace an object toward the edge of receiving member 38 and eventually fall into receptacle 12. Once the object has been displaced from receiving member 38, the biasing caused by weighted member 40 will again pivot tray 32 and receiving member 38 back into contact with shoulder 46. Additionally, while tray 32 is pivoting due to an object being deposited onto receiving member 38, sliding door member 42 is correspondingly pivoting to partially obstruct opening 18 thereby reducing the effective opening area to the inside of cover 14. This safety feature reduces the access to the interior of receptacle 12 as well as to receiving member 38 when an object is deposited thereon, thereby resisting any attempts for retrieval of disposed material.

Once receptacle 12 has been determined to be full, preferably by use of viewing windows 13, container 10 is ready to be permanently and irreversibly locked prior to removal for disposal. The locking mechanism operates in the following manner:

Tray 32 is rotated into locking position in response to the manual clockwise rotation of dial 26. Preferably, alignment of marks 52 on dial 26 and cover 14 will inform the operator that dial 26 has been rotated into proper position with locking pin 28 aligned with locking pin aperture 24. Alignment of marks 52 is shown generally in FIG. 6. Additionally, a horizontal linear ridge 54 extending outward from the surface of sliding door 42 will contact the inside surface of cover 14 just prior to the tray being rotated into locking position. Slight additional force by the operator is required to complete the clockwise rotation of dial 26 into locking position. This slight additional force is required to overcome the friction between linear ridge 54 and cover 14. The relationship between ridge 54 and cover 14 is such that ridge 54 is permitted to continue rotation past cover 14 to opening 18 but is prevented from rotating in the opposite direction and back underneath cover 14. The height of ridge 54 is therefore greater than the clearance between sliding door 42 and the inside surface of cover 14 at their closest distance to one another but not so excessively greater that the friction can not be overcome by slight additional force. After linear ridge 54 clears contact with cover 14, sliding door 42 completely closes the interior of container 10 and needle extractor 58 from opening 18 and the outside surroundings. Further, after linear ridge 54 clears contact with cover 14, sliding door 42 can not be rotated back to its original position.

Figure 10:
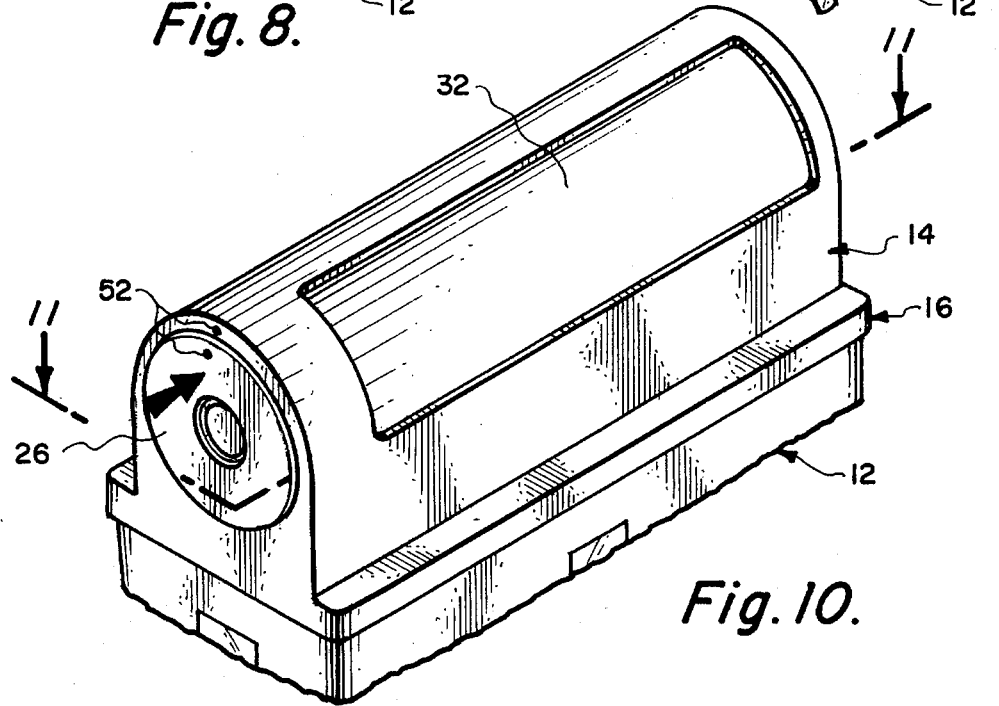
FIG. 10 is a perspective view of the cover of the invention in permanently locked position.
Figure 11:
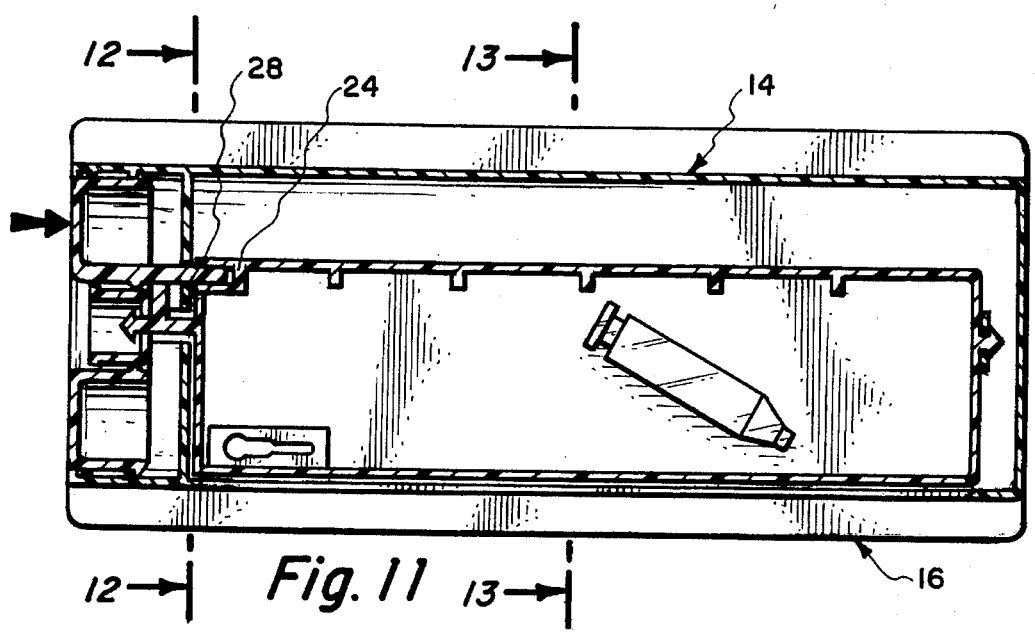
FIG. 11 is a cross-sectional view of the invention taken along line 11—11 in FIG. 10.
Figures 12, 13:
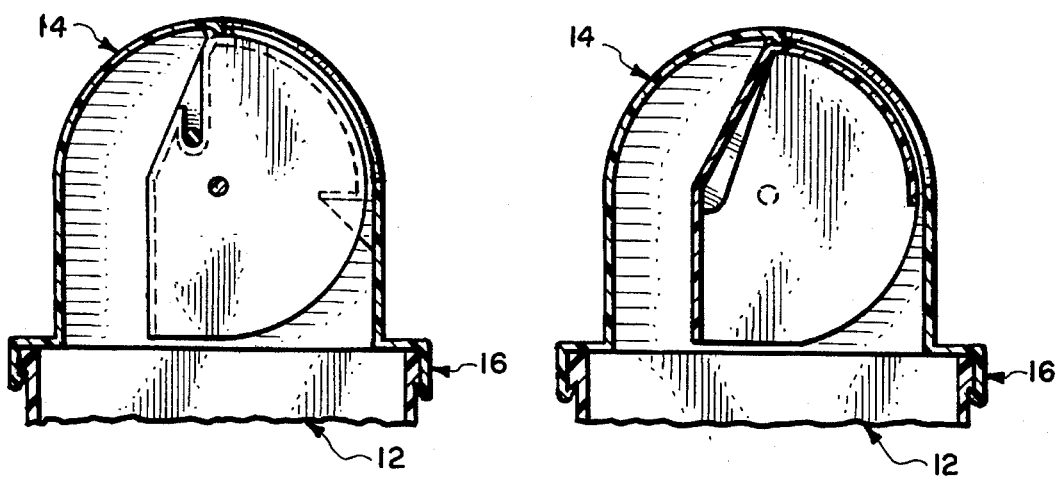
FIG. 12 is a cross-sectional view of the invention taken along line 12—12 in FIG. 11.
FIG. 13 is a cross-sectional view of the invention taken along line 13—13 in FIG. 11.

Subsequent to dial 26 being rotated clockwise into locking position using alignment marks 52, dial 26 is displaced into cover 14 as is shown generally in FIG. 10. As force is applied to displace dial 26 into cover 14, frangible connectors 31 fail and the connection between dial cylinder receiving recess 29 and dial cylinder 30 is severed permitting displacement of dial 26 completely into dial recess 20 and correspondingly displacement of dial cylinder 30 into dial cylinder receiving recess 29 and locking pin 28 into locking pin aperture 24. More particularly, as dial 26 is further displaced into dial recess 20, ridge 48 about the circumference of dial 26 is displaced past a second dial recess shoulder 56. Second dial recess shoulder 56 is similar in function as first dial recess shoulder 50 in that it permits movement of ridge 48 further into cover 14 but prevents movement of ridge 48 in the opposite direction. Once ridge 48 has been displaced inward past second dial recess shoulder 56, the exterior top surface of dial 26 becomes substantially flush with the adjacent exterior surface of cover 14 and is no longer accessible for manual rotation, which would in any event be prevented by the locking pin 28.

While the presently preferred form of the invention has been disclosed in detail in order to comply with the requirements of the patent laws, it will be understood by those skilled in the art that many variations and alternatives are possible within the spirit and the teaching of the present invention.

What we claim is:

1. A sharps container comprising:

a receptacle for receiving sharps, a cover connected to said receptacle in such a manner as to define an inner space between said receptacle and said cover, said cover further having a dial recess and an opening for receiving sharps into said receptacle;

a dial partially disposed within said dial recess, moveably and rotatably mounted to said cover;

an elongated tray disposed in said cover, said tray rotatable about a horizontal axis between receiving, partially closed and locking positions, said receiving position for receiving sharps through said opening while closing access to said receptacle interior is closed, said partially closed position for displacement of sharps into said receptacle interior, while partially obstructing said opening to said container, and said locking position for engagement of a locking means for permanently closing said container, said tray biased into said receiving position, said tray overcoming said bias and rotate to a partially closed position when an object is placed onto said tray, said tray rotates in a direction opposite of said bias until said object falls by force of gravity into said interior, whereupon said bias rotates said tray back to said receiving position, said tray further rotatable to said locking position in response to manual rotation of said dial, said container being completely closed when said tray is in said locking position; and said locking means including a locking pin aperture located in said cover, a locking pin which extends from said dial and which is movable between a first position wherein said locking pin is removed from said locking pin aperture and said dial is partially removed from said dial recess and a second position wherein said dial is manually moveable into locking engagement with said dial recess thereby moving said locking pin into said locking pin aperture when said dial has been rotated into said locking position.

2. A sharps container apparatus as in claim 1 wherein said locking means includes interengaging means on said dial and on said cover for securing said dial in said second position.

3. A sharps container apparatus as in claim 1 wherein the exposed surface of said dial in said second position is substantially flush with the adjacent exterior surface of said cover.

4. A sharps container as recited in claim 1 wherein said locking means further comprises a linear ridge on the backside of said tray partially extending the longitudinal length of said tray for engaging an edge of said cover defining a boundary of said opening when said opening is completely isolated from the interior of said container by the rotation of said tray into said locking position.

5. A sharps container as recited in claim 1 wherein said container is comprised of a puncture resistant material.

6. A sharps container as recited in claim 5 wherein said container is comprised of a puncture resistant plastic material.

7. A sharps container as recited in claim 6 wherein said puncture resistant plastic material is a propylene random co-polymer.

8. A sharps container as recited in claim 1 wherein said receptacle further comprises a viewing window to permit visual inspection of said interior of said receptacle.

9. A sharps container as recited in claim 8 wherein said viewing window comprises a puncture resistant material.

* * * * *